US011248250B2

(12) United States Patent
Fryer et al.

(10) Patent No.: US 11,248,250 B2
(45) Date of Patent: Feb. 15, 2022

(54) SELF-CONTAINED BIOLOGICAL INDICATOR (71) Applicant: ASP Global Manufacturing GmbH, Schaffhausen (CH)

(72) Inventors: Ben Fryer, Lake Forest, CA (US); Yan Fang, Irvine, CA (US)

(73) Assignee: ASP GLOBAL MANUFACTURING GMB, Schaffhausen (CH)

(*) Notice: Subject to any disclaimer, the term of this patent is extended or adjusted under 35 U.S.C. 154(b) by 630 days.

(21) Appl. No.: 15/828,563

(22) Filed: Dec. 1, 2017

(65) Prior Publication Data
US 2019/0169672 A1 Jun. 6, 2019

(51) Int. Cl.
C12M 1/12 (2006.01)
C12Q 1/22 (2006.01)
A61L 2/28 (2006.01)
C12Q 1/04 (2006.01)
C12M 1/34 (2006.01)

(52) U.S. Cl.
CPC .......... C12Q 1/22 (2013.01); A61L 2/28 (2013.01); C12Q 1/04 (2013.01); C12M 1/3476 (2013.01); C12M 37/06 (2013.01)

(58) Field of Classification Search
CPC ....... A61L 2/28; C12M 1/3476; C12M 37/06; C12Q 1/04; C12Q 1/22; G01N 21/78; G01N 21/6428
USPC ...................................................... 435/287.4
See application file for complete search history.

(56) References Cited

U.S. PATENT DOCUMENTS

| 3,346,464 | A | | 10/1967 | Ernst |
| 3,752,743 | A | | 8/1973 | Henshilwood |
| 3,948,727 | A | | 4/1976 | Steiger |
| 4,291,122 | A | | 9/1981 | Orelski |
| 4,304,869 | A | | 12/1981 | Dyke |
| 4,528,268 | A | | 7/1985 | Andersen et al. |
| 4,546,086 | A | * | 10/1985 | Hounsell ............... C12M 23/34 422/236 |
| 4,717,661 | A | | 1/1988 | McCormick et al. |
| 4,732,850 | A | | 3/1988 | Brown et al. |
| 4,741,437 | A | | 5/1988 | Gorski et al. |

(Continued)

FOREIGN PATENT DOCUMENTS

| CA | 738687 A | 7/1966 |
| CA | 823163 A | 9/1969 |

(Continued)

OTHER PUBLICATIONS

US 8,945,737 B2, 02/2015, Franciskovich et al. (withdrawn)

(Continued)

Primary Examiner — Liban M Hassan
(74) Attorney, Agent, or Firm — Etan S. Chatlynne; Roberts Calderon Safran & Cole P.C.

(57) ABSTRACT

A self-contained biological indicator ("SCBI") is disclosed. The SCBI may include a first ampule and a second ampule. The first ampule may contain a first volume of a first growth medium, and the second ampule may contain a second volume of a second growth medium. The SCBI is configured such that the first ampule may be broken before the second ampule. The SCBI may be analyzed for changes in fluorescence of the first growth medium. Then, the SCBI may be analyzed for changes in a color of the second growth medium.

16 Claims, 4 Drawing Sheets

(56) References Cited

U.S. PATENT DOCUMENTS

| | | | |
|---|---|---|---|
| 4,839,291 A | 6/1989 | Welsh et al. | |
| 4,883,641 A | 11/1989 | Wicks et al. | |
| 4,885,253 A | 12/1989 | Kralovic | |
| 5,028,543 A * | 7/1991 | Finch | B01L 3/508 208/2 |
| 5,073,488 A | 12/1991 | Matner et al. | |
| 5,167,923 A | 12/1992 | Van Iperen | |
| 5,223,401 A | 6/1993 | Foltz et al. | |
| 5,252,484 A | 10/1993 | Matner et al. | |
| 5,362,654 A * | 11/1994 | Pouletty | C23C 16/487 422/430 |
| 5,405,580 A | 4/1995 | Palmer | |
| 5,415,994 A * | 5/1995 | Imrich | B01L 3/5023 435/5 |
| 5,418,167 A | 5/1995 | Matner et al. | |
| 5,482,171 A | 1/1996 | Palmer | |
| 5,516,648 A | 5/1996 | Malchesky et al. | |
| 5,552,320 A | 9/1996 | Smith | |
| 5,736,355 A | 4/1998 | Dyke et al. | |
| 5,739,004 A | 4/1998 | Woodson | |
| 5,750,184 A | 5/1998 | Imburgia | |
| 5,759,848 A | 6/1998 | Nagoshi et al. | |
| 5,770,393 A | 6/1998 | Dalmasso et al. | |
| 5,801,010 A | 9/1998 | Falkowski et al. | |
| 5,830,683 A | 11/1998 | Hendricks et al. | |
| 5,863,790 A | 1/1999 | Bolea | |
| 5,866,356 A | 2/1999 | Albert et al. | |
| 5,942,438 A | 8/1999 | Antonoplos et al. | |
| 6,218,189 B1 | 4/2001 | Antonoplos et al. | |
| 6,436,659 B1 | 8/2002 | Hui et al. | |
| 6,458,554 B1 | 10/2002 | Hui et al. | |
| 6,551,555 B2 | 4/2003 | Antonoplos et al. | |
| 6,924,139 B2 | 8/2005 | Eveland et al. | |
| 7,091,042 B2 | 8/2006 | Lemus et al. | |
| 7,247,482 B2 | 7/2007 | Lemus et al. | |
| 7,642,067 B2 | 1/2010 | Song et al. | |
| 8,173,388 B2 | 5/2012 | Pasmore et al. | |
| 8,173,438 B1 | 5/2012 | Putnam et al. | |
| 8,765,398 B2 | 7/2014 | Dalmasso | |
| 8,840,837 B2 | 9/2014 | Smith et al. | |
| 8,915,413 B2 | 12/2014 | Kayser | |
| 8,969,029 B2 | 3/2015 | Chandrapati et al. | |
| 8,980,622 B2 | 3/2015 | Smith | |
| 9,145,573 B2 | 9/2015 | Pederson et al. | |
| 9,322,046 B2 | 4/2016 | Chandrapati et al. | |
| 9,675,722 B2 | 6/2017 | Ahimou et al. | |
| 10,059,977 B2 | 8/2018 | Witcher et al. | |
| 2004/0197848 A1 | 10/2004 | Behun et al. | |
| 2005/0014214 A1 | 1/2005 | Eveland et al. | |
| 2008/0070272 A1 | 3/2008 | Franciskovich et al. | |
| 2009/0068716 A1 | 3/2009 | Hirota et al. | |
| 2011/0200992 A1 | 8/2011 | Chandrapati et al. | |
| 2012/0149094 A1 * | 6/2012 | Smith | A61L 2/28 435/288.7 |
| 2012/0156090 A1 | 6/2012 | Dane et al. | |
| 2013/0210048 A1 | 8/2013 | Chandrapati et al. | |
| 2013/0217107 A1 | 8/2013 | Pederson et al. | |
| 2013/0224849 A1 * | 8/2013 | Chandrapati | C12Q 1/22 435/287.4 |
| 2013/0273594 A1 | 10/2013 | Ahimou et al. | |
| 2015/0004682 A1 | 1/2015 | Smith et al. | |
| 2015/0167047 A1 | 6/2015 | Smith et al. | |
| 2015/0337354 A1 | 11/2015 | Ahimou et al. | |
| 2016/0000954 A1 | 1/2016 | Ahimou et al. | |
| 2017/0175071 A1 | 6/2017 | Sullivan et al. | |
| 2017/0211035 A1 | 7/2017 | Yirava et al. | |
| 2017/0253845 A1 | 9/2017 | Behnam | |
| 2018/0015193 A1 | 1/2018 | Swaminathan et al. | |
| 2018/0071421 A1 | 3/2018 | Fang et al. | |
| 2018/0187142 A1 | 7/2018 | Troung | |
| 2018/0237821 A1 | 8/2018 | Fryer | |
| 2019/0002951 A1 | 1/2019 | Fryer et al. | |
| 2019/0106725 A1 | 4/2019 | Cregger et al. | |
| 2019/0106726 A1 | 4/2019 | Cregger et al. | |
| 2019/0169672 A1 | 6/2019 | Fryer et al. | |

FOREIGN PATENT DOCUMENTS

| | | |
|---|---|---|
| CA | 1 182 729 A | 2/1985 |
| CN | 1853734 A | 11/2006 |
| CN | 201453688 U | 5/2010 |
| CN | 102596261 A | 7/2012 |
| CN | 203307339 U | 11/2013 |
| CN | 105087361 A | 11/2015 |
| CN | 204814967 U | 12/2015 |
| CN | 105561362 A | 5/2016 |
| CN | 106267277 A | 1/2017 |
| CN | 206473580 U | 9/2017 |
| CN | 206970617 U | 2/2018 |
| EP | 0 152 298 A2 | 8/1985 |
| EP | 1032822 B1 | 5/2003 |
| EP | 2968634 B1 | 12/2016 |
| FR | 2708287 B1 | 10/1995 |
| GB | 1055387 A | 1/1967 |
| IN | 201747012748 A | 4/2017 |
| IN | 201714046902 A | 7/2018 |
| JP | 10201466 A | 8/1998 |
| JP | 11196893 A | 7/1999 |
| JP | 2017123976 A | 7/2017 |
| JP | 2018201397 A | 12/2018 |
| RU | 129814 U1 | 7/2013 |
| RU | 143648 U1 | 7/2014 |
| RU | 146719 U1 | 10/2014 |
| RU | 2683644 C2 | 4/2019 |
| WO | 92/19764 A1 | 11/1992 |
| WO | 97/35189 A1 | 9/1997 |
| WO | 00/50634 A1 | 8/2000 |
| WO | 2005/036128 A2 | 4/2005 |
| WO | 2010/039388 A2 | 4/2010 |
| WO | 2010/045138 A2 | 4/2010 |
| WO | 2016/057520 A1 | 4/2016 |
| WO | 2016/205953 A1 | 12/2016 |
| WO | 2018025207 A1 | 2/2018 |
| WO | 2018/160449 A1 | 9/2018 |
| WO | 2008106327 A2 | 9/2018 |
| WO | 2020/136463 A1 | 7/2020 |

OTHER PUBLICATIONS

Namsa, Self-Contained Biological Indicators For Monitoring Steam (Northwood, Ohio, 2015).

Anonymous, 3M™ Attest™ 1292E Rapid Readout Biological Indicator, Internet Article, Jan. 1, 1999, http://multimedia.3m.com/mws/mediawebserver?mwsId=SSSSSu7zK1fsIxtU48_eI8mGev7qe17zHvTSevTSeSSSSSS--&fn=Rapid_Readout_Profile_1292E.pdf.

PCT Notification of Transmittal of the International Search Report and the Written Opinion of the International Searching Authority, or the Declaration for International Application No. PCT/IB2020/058750 dated Nov. 27, 2020, 1 page.

PCT Written Opinion of the International Searching Authority for International Application No. PCT/IB2020/058750 dated Nov. 27, 2020, 6 pages.

PCT International Search Report for International Application No. PCT/IB2020/058750 dated Nov. 27, 2020, 6 pages.

Chinese First Office Action and Search Report for Chinese Patent Application No. 201810004516.1 dated Aug. 3, 2020 and English translation.

Russian Search Report for Registration No. 2017145872/04(078515) dated Dec. 26, 2017, Date of valid search completion: Jun. 10, 2021, 2 pages.

\* cited by examiner

SELF-CONTAINED BIOLOGICAL INDICATOR

CROSS-REFERENCE TO CO-PENDING APPLICATION

This application is a counterpart of U.S. patent application Ser. No. 15/057,768, filed Mar. 1, 2016, and Ser. No. 15/397,018, filed Jan. 31, 2017, both of which are incorporated by reference their entirety.

FIELD

The subject matter disclosed herein relates to self-contained biological sterilization indicators.

BACKGROUND

A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms possessing known resistance to the sterilant may be placed into a sterilization chamber alongside a medical device and subjected to a sterilization cycle. After the cycle is complete, the microorganisms in the biological indicator may be cultured to determine whether any of the microorganisms survived the cycle.

Certain biological indicators are referred to as being "self-contained." These biological indicators typically include a housing that contains a quantity of microorganisms and a source of growth media in a frangible container that is located near the microorganisms. Like other biological indicators, the "self-contained" biological indicator ("SCBI") may be subject to a sterilization cycle alongside medical devices. Following the cycle, the frangible container may be broken to release the growth media and culture any surviving microorganisms in situ. The SCBI may be incubated at elevated temperatures, typically around 50° C. to 60° C., which encourages outgrowth of the surviving microorganisms.

After incubation, the SCBI is analyzed to detect the presence of microorganisms. Should any microorganisms be detected, the sterilization cycle may be considered to have been ineffective. Should no microorganisms be detected, the sterilization cycle may be considered to have been effective. Some SCBIs are designed to incorporate a growth medium that changes color in the presence of microorganisms. This color change may be due to a shift in pH that occurs due to acid production by live microorganisms that metabolize a growth medium, which also contains a pH indicating dye. Other SCBIs are designed to incorporate a growth medium that includes a fluorophore whose fluorescence depends on the amount of viable microorganisms contained in the medium. For these SCBIs, a color change or change in the amount of fluorescence indicates that surviving microorganisms may have multiplied during incubation.

SUMMARY

A self-contained biological indicator ("SCBI") is disclosed. The SCBI may include a first ampule having a first top and a first bottom. The SCBI may also include a second ampule having a second top and a second bottom. The first ampule may contain a first volume of a first growth medium, and the second ampule may contain a second volume of a second growth medium. The first ampule may be disposed adjacent to the second ampule. The SCBI may also include a cap, which may be disposed above the first ampule and the second ampule. The first top of the first ampule may be disposed closer to the cap than the second top of the second ampule. In some embodiments, the first top may contact the cap. The SCBI may also include an insert, at least a portion of which may be disposed below and in contact with the first ampule and the second ampule.

In some embodiments, the first ampule may be longer than the second ampule. For example, the first ampule may be between approximately 0.5 inches and 1.5 inches longer than the second ampule. The first ampule may be approximately 1 inch longer than the second ampule. In some embodiments, the insert may include a first surface and a second surface that is parallel or substantially parallel to the first surface and further from the cap than the first surface. In these embodiments, the first bottom may contact the first surface and the second bottom may contact the second surface. The first surface may be disposed between approximately 0.1 inches to 1.5 inches above the second surface. The first surface may be disposed approximately 0.8 inches above the second surface.

In some embodiments, the first growth medium is the same as the second growth medium. For example, the first growth medium and the second growth medium may include 4-methylumbelliferyl α-D-glucoside (MUG). The first volume of the first growth medium may be less than the second volume of the second growth medium. The first volume may be between approximately 50 µl and 150 µl and the second volume may be greater than approximately 150 µl. The first volume may be approximately 100 µl and the second volume may be approximately 300 µl.

The SCBI may also include a vial coupled to the cap. At least a portion of the first ampule and a portion of the second ampule may be disposed within the vail. The vial and cap may include tongue and a groove features. The vial may alternatively or additionally include a stop surface surrounding a portion of the vial and disposed between approximately 0.1 inches and 1.5 inches below a rim of the cap. For example, the stop surface may be disposed approximately 0.8 inches from the rim of the cap.

The SCBI may be used to determine whether a sterilization cycle is efficacious. The SCBI may be subjected to the sterilization cycle. Then, the first ampule may be broken. The SCBI may be analyzed for changes in fluorescence of the first growth medium. Then, the second ampule may be broken. The SCBI may be analyzed for changes in a color of the second growth medium. In some exemplary versions of this method, the step of breaking the first ampule includes depressing the cap from the first position toward a second position, and the step of breaking the second ampule includes depressing the cap from the second position toward a third position.

BRIEF DESCRIPTION OF THE DRAWINGS

While the specification concludes with claims which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Self-contained biological indicators ("SCBIs") have been described, for example in co-pending U.S. patent application Ser. Nos. 15/057,768 and 15/397,018, which are incorporated by reference herein in their entirety. SCBIs that may be quickly analyzed to assess the efficacy of a sterilization cycle provide certain commercial advantages over those that must be analyzed more slowly. Specifically, they permit healthcare personnel to process and confirm sterility of medical instruments more quickly, which in turn assists a healthcare facility efficiently utilize its inventory of medical instruments. To assist in achieving a fast read, certain SCBIs require use of a secondary device, such as a computerized reading device. For example, the Applicant, Advanced Sterilization Products, Division of Ethicon US, LLC, located in Irvine Calif., recently launched the STERRAD® Velocity™ Biological Indicator System, which includes an SCBI and a reading device (or reader) that is capable of incubating the SCBI and determining sterilization efficacy in under thirty minutes.

The STERRAD VELOCITY™ Biological Indicator is an SCBI that contains a spore disc in a growth reservoir, which carries over one million *Geobacillus stearothermophilus* [ATCC 7953] spores. These spores have been identified as the most resistant known organism for challenging hydrogen peroxide based sterilization systems. This SCBI also contains a glass ampule filled with liquid growth medium designed to promote the growth of *G. stearothermophilus*. These components are contained in a clear plastic vial with a vented cap. The cap is designed with sterilant ingress windows which allow sterilant to enter the vial during the sterilization process, and then seal when activated for reading. Upon activation, the ampule breaks and the growth medium fills the growth reservoir.

The α-glucosidase enzyme is generated naturally during growth of *G. stearothermophilus* and released during spore germination. The α-glucosidase enzyme in its active state is detected by measuring the fluorescence produced by the enzymatic hydrolysis of a nonfluorescent substrate, 4-methylumbelliferyl α-D-glucoside (MUG). The resultant fluorescent by-product, 4-methylumbelliferone (MU), is detected in the reader. The fluorescent signal is used to determine the positive or negative result of the SCBI.

SCBIs that may be analyzed using a reader capable of measuring and monitoring fluorescence, such as the STERRAD VELOCITY™ SCBI, may also provide for a secondary or "backup" mode of analysis, which may be considered an optional confirmation or substitute process for confirming efficacy of a sterilization process. For example, results may be visually interpreted by healthcare personnel. To do so, healthcare personnel may incubate a processed SCBI (i.e., an SCBI that was subject to a sterilization procedure), and perhaps a control SCBI (i.e., an SCBI that was not subject to a sterilization procedure), at 55-60° C. (131-140° F.) for 5 to 7 days. After incubation, the growth medium in the processed SCBI may be visually inspected for a color change and, optionally, compared to a control SCBI. The absence of a color change of the growth medium in the processed BI indicates that the sterilization cycle should be efficacious. For example, if the growth medium was originally purple and it remains purple following the incubation, the sterilization cycle should be efficacious. However, a change, e.g., from purple to yellow of the growth medium in the processed BI indicates that the sterilization process likely was not efficacious.

The inventors have discovered that when a sterilization determination is based on monitoring fluorescent byproducts within an SCBI, the volume of growth medium present in the growth reservoir is inversely proportional to the amount of time required for the reader to determine the result. That is, the rate of change in fluorescence caused by spore outgrowth is reduced by larger volumes of fluid. Accordingly, for lesser volumes of fluid, detection of fluorescence may be facilitated such that sterilization results may be determined more quickly. The growth reservoir of the STERRAD VELOCITY™ SCBI has a volume of approximately 300 μl. When the growth reservoir is filled with growth medium, i.e., about 300 μl of the growth medium, determination of the sterilization result takes up to about thirty minutes. However, for example, when the growth reservoir is not filled, but is only partially filled, determination of the sterilization result takes less than about thirty minutes. For example, when approximately 100 μl of growth medium is in the growth reservoir, determination of the sterilization result takes up to only about ten minutes, which is significantly faster than thirty minutes.

Use of a smaller volume of growth medium, e.g., approximately 200 μl or less, may not be compatible with those procedures that include a backup or optional visual interpretation of the color of the SCBI's growth medium following days of incubation because during the course of the incubation, the growth medium may evaporate substantially or entirely. Such evaporation may hinder or prevent healthcare personnel from performing the visual interpretation of color change.

Figure 1:
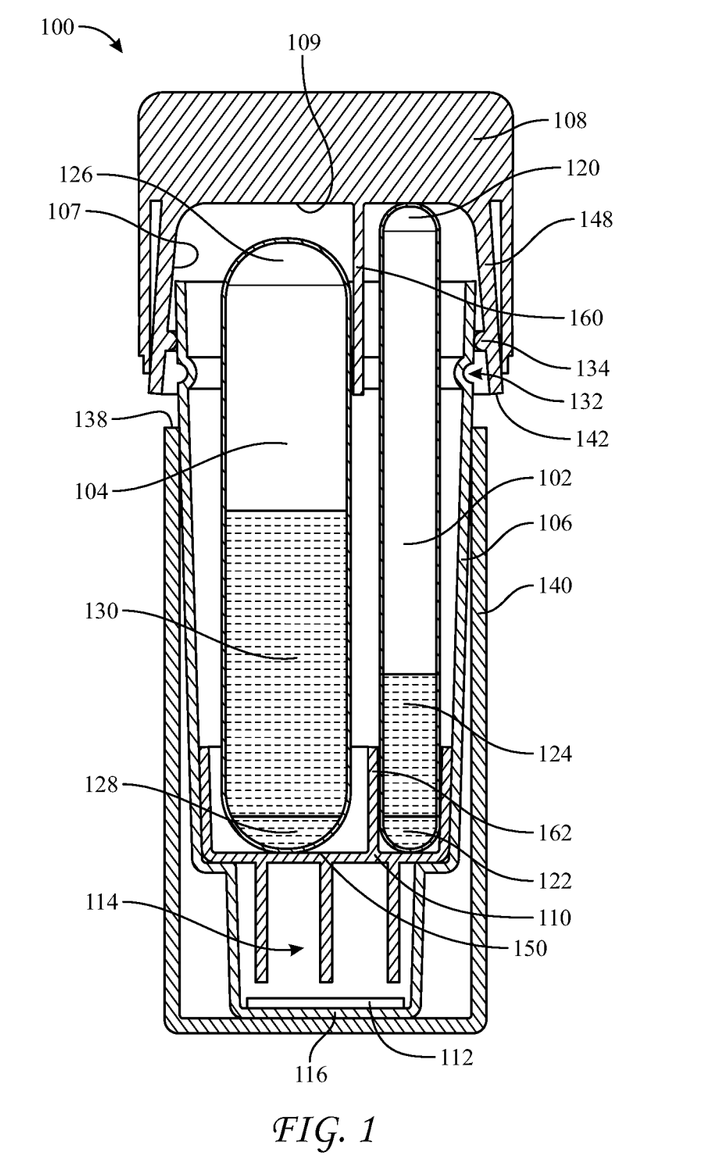
FIG. 1 depicts a cross-sectional view of a self-contained biological indicator with a cap in a first position.
Figure 2:
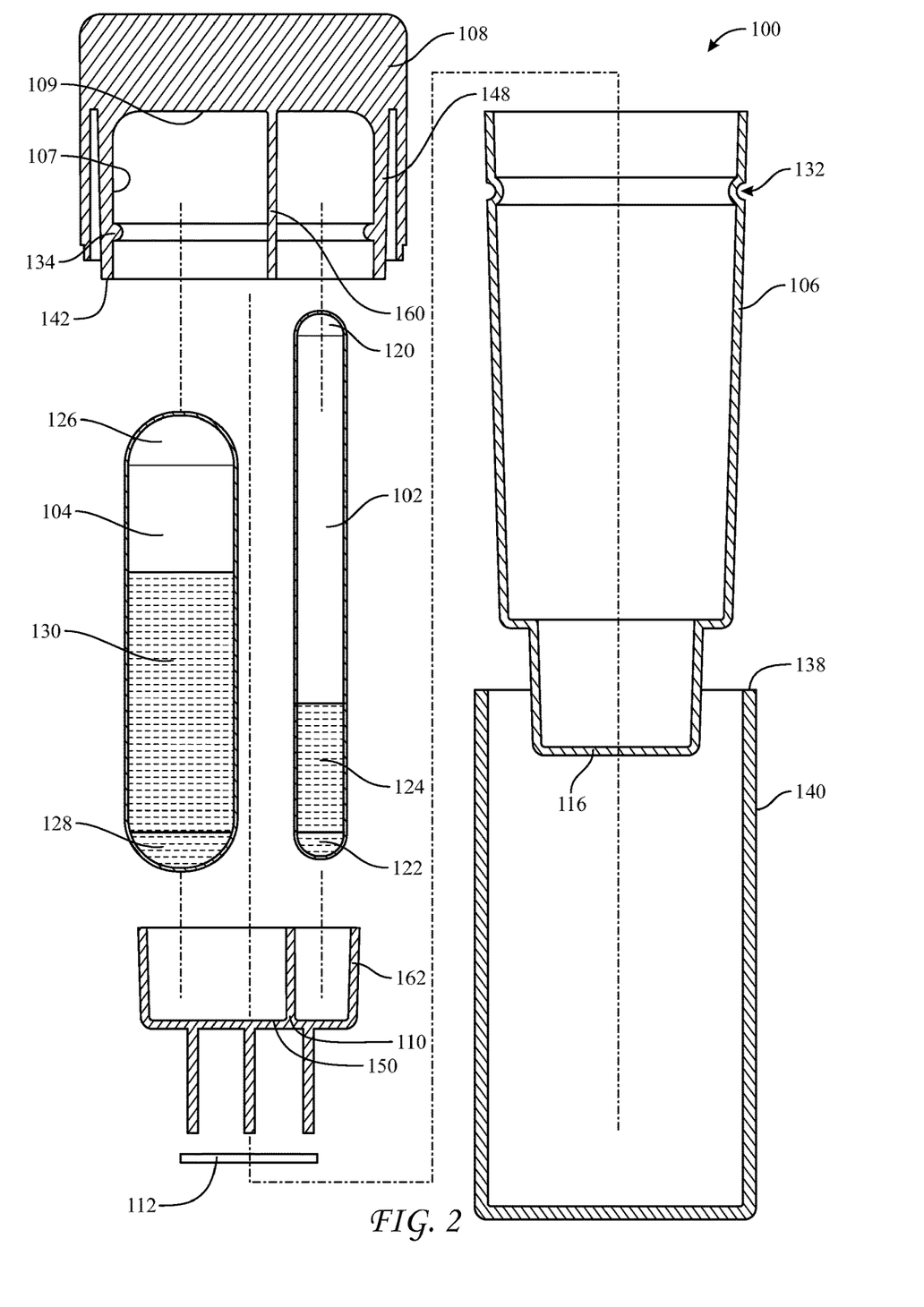
FIG. 2 depicts an exploded cross-sectional view of the self-contained biological indicator of FIG. 1.

FIGS. 1 and 2 show SCBI 100, which is designed to allow a rapid determination of sterility based on analyzing fluorescence using a reader while avoiding the possibility that a user will be unable to perform a visual interpretation of color change. SCBI 100 includes two ampules, a first ampule 102 and a second ampule 104. First ampule 102 includes a first top 120, a first bottom 122, and a first growth medium 124. Second ampule 104 includes a second top 126, a second bottom 128, and a second growth medium 130. First ampule 102 and second ampule 104 may be disposed adjacent to each other within a vial 106 of SCBI 100. Growth media 124 and 126 may include enzymes, a source of enzymes, and/or enzyme substrates.

Enzymes and enzyme substrates that may be used to detect efficacy of a sterilization cycle are identified in U.S. Pat. No. 5,073,488, entitled "Rapid Method for Determining Efficacy of a Sterilization Cycle and Rapid Read-Out Biological Indicator," issued Dec. 17, 1991, the disclosure of which is incorporated by reference in its entirety herein; U.S. Pat. No. 5,418,167, entitled "Rapid Read-Out Biological Indicator," issued May 23, 1995, the disclosure of which is incorporated by reference in its entirety herein; U.S. Pat. No. 5,223,401, entitled "Rapid Read-Out Sterility Indicator," issued Jun. 29, 1993, the disclosure of which is incorporated by reference herein; and U.S. Pat. No. 9,322,046, entitled "Biological Sterilization Indicator," issued Apr. 26, 2016, the disclosure of which is incorporated by reference in its entirety herein.

Suitable enzymes may include hydrolytic enzymes and/or enzymes derived from spore-forming microorganisms, such as *Bacillus subtilis*. Enzymes from spore-forming microorganisms that can be useful in exemplary biological indicators may include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase, fatty acid esterases and combinations thereof.

In some exemplary methods for determining efficacy of a sterilization cycle as disclosed herein, enzyme substrates are converted to detectable product. For instance, an enzyme substrate may be characterized by a first emission spectrum (e.g., a first fluorescent emission spectrum) and a detectable product may be characterized by a second emission spectrum (e.g., a second fluorescent emission spectrum).

In some exemplary methods for determining efficacy of a sterilization cycle as disclosed herein, suitable enzyme substrates of use may include fluorogenic enzyme substrates. Useful fluorogenic enzyme substrates may be selected from: fluorogenic 4-methylumbelliferyl derivatives (hydrolysable to 4-methylumbelliferone ("4-Mu"), derivatives of 7-amido-4-methyl-coumarin, diacetylfluorescein derivatives, fluorescamine and combinations thereof.

Exemplary 4-methylumbelliferyl derivatives may be selected from: 4-methylumbelliferyl-2-acetamido-4,6-O-benzylidene-2-deoxy-β-D-glucopyranoside, 4-methylumbelliferyl acetate, 4-methylumbelliferyl-N-acetyl-β-D-galactosaminide, 4-methylumbelliferyl-N-acetyl-α-D-glucosaminide, 4-methylumbelliferyl-N-acetyl-β-D-glucosaminide, 2'-(4-methylumbelliferyl)-α-D-N-acetyl neuraminic acid, 4-methylumbelliferyl α-L-arabinofuranoside, 4-methylumbelliferyl α-L-arabinoside, 4-methylumbelliferyl butyrate, 4-methylumbelliferyl 13-D-cellobioside, methylumbelliferyl β-D-N,N' diacetyl chitobioside, 4-methylumbelliferyl elaidate, 4-methylumbelliferyl β-D-fucoside, 4-methylumbelliferyl α-L-fucoside, 4-methylumbelliferyl β-L-fucoside, 4-methylumbelliferyl α-D-galactoside, 4-methylumbelliferyl β-D-galactoside, 4-methylumbelliferyl α-D-glucoside, 4-methylumbelliferyl β-D-glucoside, 4-methylumbelliferyl β-D-glucuronide, 4-methylumbelliferyl p-guanidinobenzoate, 4-methylumbelliferyl heptanoate, 4-methylumbelliferyl α-D-mannopyranoside, 4-methylumbelliferyl β-D-mannopyranoside, 4-methylumbelliferyl oleate, 4-methylumbelliferyl palmitate, 4-methylumbelliferyl phosphate, 4-methylumbelliferyl propionate, 4-methylumbelliferyl stearate, 4-methylumbelliferyl sulfate, 4-methylumbelliferyl β-D-N,N',N"-triacetylchitotriose, 4-methylumbelliferyl 2,3,5-tri-o-benzoyl-α-L-arabinofuranoside, 4-methylumbelliferyl-p-trimethylammonium cinnamate chloride, 4-methylumbelliferyl β-D-xyloside and combinations thereof.

In certain embodiments, the fluorescent response in the SCBI may be based on the naturally occurring alpha-glucosidase enzyme found in the *Geobacillus stearothermophilus* spore coat, which contains the enzyme and which is believed to be important in the germination of *G. stearothermophilus*. Alpha-glucosidase may be used to hydrolyze the bond between the glucose and 4-methylumbelliferyl moieties of 4-methylumbelliferyl α-D-glucopyranoside (α-MUG). α-MUG is not fluorescent. However, following hydrolyzation and separation of the moieties, the 4-Methylumbelliferone (4-MU) product is fluorescent. 4-MU fluoresces when excited by an external energy source, such as a light source that emits light having a wavelength of between approximately 360 and 370 nanometers. So excited, 4-MU emits light having a wavelength of between approximately 440 and 460 nanometers.

SCBI 100 also includes a cap 108. Cap 108 includes an inner side surface 107 and an inner top surface 109, and an annular projection 148. Cap 108 is disposed atop vial 106 in a first or unactivated position and is configured to be movable from the first position to a second position, and from the second position to a third position. SCBI 100 should be further configured such that movement of cap 108 from the first position to the second position breaks first ampule 102 and such that movement of cap 108 from the second position to the third position breaks second ampule 104. SCBI 100 also includes an insert 110, a spore disk 112, and a growth reservoir 114, which may be a volume defined by a bottom portion of vial 106. Spore disk 112 is disposed on a base 116 of growth reservoir 114. Insert 110 is disposed above spore disk 112. In some embodiments, first ampule 102 and second ampule 104 are disposed upon and in contact with a surface 150 of insert 110 that is parallel or substantially parallel to inner top surface 109 of cap 108.

By incorporating two separate volumes of growth media into SCBI 100, i.e., first growth medium 124 in first ampule 102 and second growth medium 130 in second ampule 104, a quick (e.g., twenty minutes or less) fluorescence-based assessment of sterilization may be accomplished and the evaporation problem described above may be circumvented. Specifically, first growth medium 124 includes a substrate that produces a fluorescent byproduct that can be monitored by a reader. First growth medium 124 is provided in first ampule 102, which may be broken before second ampule 104. Second ampule 104 may thus be broken at a later time, e.g., after fluorescence detections and sterility determinations have been made by the reader. Second ampule 104, which may have a volume of second growth medium 130 sufficiently large to avoid complete or substantial evaporation during incubation, may be broken after use of the reader and fluorescence determinations are complete. Alternatively, if a healthcare worker does not use a reader to monitor fluorescence (e.g., because she does not have one or because she would prefer not to use one), the healthcare worker may break second ampule 104 promptly after breaking first ampule 102 and begin incubation in anticipation of visual interpretation.

In some embodiments, first growth medium 124 and second growth medium 130 are the same growth medium, such as a growth medium that contains a nonfluorescent substrate, e.g., 4-methylumbelliferyl α-D-glucoside (MUG), which, when exposed to an enzyme, such as α-glucosidase, releases a fluorescent byproduct 4-methylumbelliferone (MU). In some embodiments first growth medium 124 and second growth medium 130 may be different growth media. The growth media may be different because visual interpretation of results does not rely on fluorescent properties of the medium. Accordingly, a substrate with a fluorescent byproduct need not be included in second growth medium 130. In some embodiments the volume of growth medium 124 and growth medium 130 is the same. For example, the volume in each ampule may be, e.g., between approximately 100 μl and 300 µl. In certain embodiments, the volume in each ampule may be 200 µl. In other embodiments, the volume of first growth medium 124 may be less than the volume of second growth medium 130. For example, the volume of first growth medium 124 may be between approximately 50 µl and 150 µl and the volume of second growth medium 130 may be greater than approximately 150 µl. In certain embodiments, the volume of first growth medium 124 may be approximately 100 µl and the volume of second growth may be approximately 300 µl.

In some embodiments, first top 120 may be disposed closer to cap 108 than second top 126. In some embodiments, first top 120 may contact cap 108. Thus, in some embodiments, and as shown in FIGS. 1 and 2, first ampule 102 may be longer or taller than second ampule 104. Therefore, activation of SCBI 100 by depressing cap 108 causes first ampule 102 to break before second ampule 104. In some embodiments, first ampule 102 may be between approximately 0.5 inches and 1.5 inches longer than second ampule 104. In certain embodiments, first ampule 102 may be approximately 1 inch longer than second ampule 102.

Various embodiments may include features to avoid premature breakage of first ampule 102 and second ampule 104. For example, a cap partition 160 may be included as a feature of cap 108. Specifically, cap partition 160 may project from inner top surface 109 of cap 108 toward the bottom of vial 106. Cap partition 160 may be centered or off-centered within cap 108 and disposed between first top 120 and second top 126 to maintain separation between first ampule 102 and second ampule 104. Similarly, an insert partition 162 may be included as a feature of insert 110. Specifically, insert partition 162 may project from surface 150 of insert 110 toward the top of vial 106. Insert partition 162 may be centered or off-centered within insert 110, or aligned with cap partition 160, and disposed between first bottom 122 and second bottom 128 to maintain separation between first ampule 102 and second ampule 104.

Figure 3:
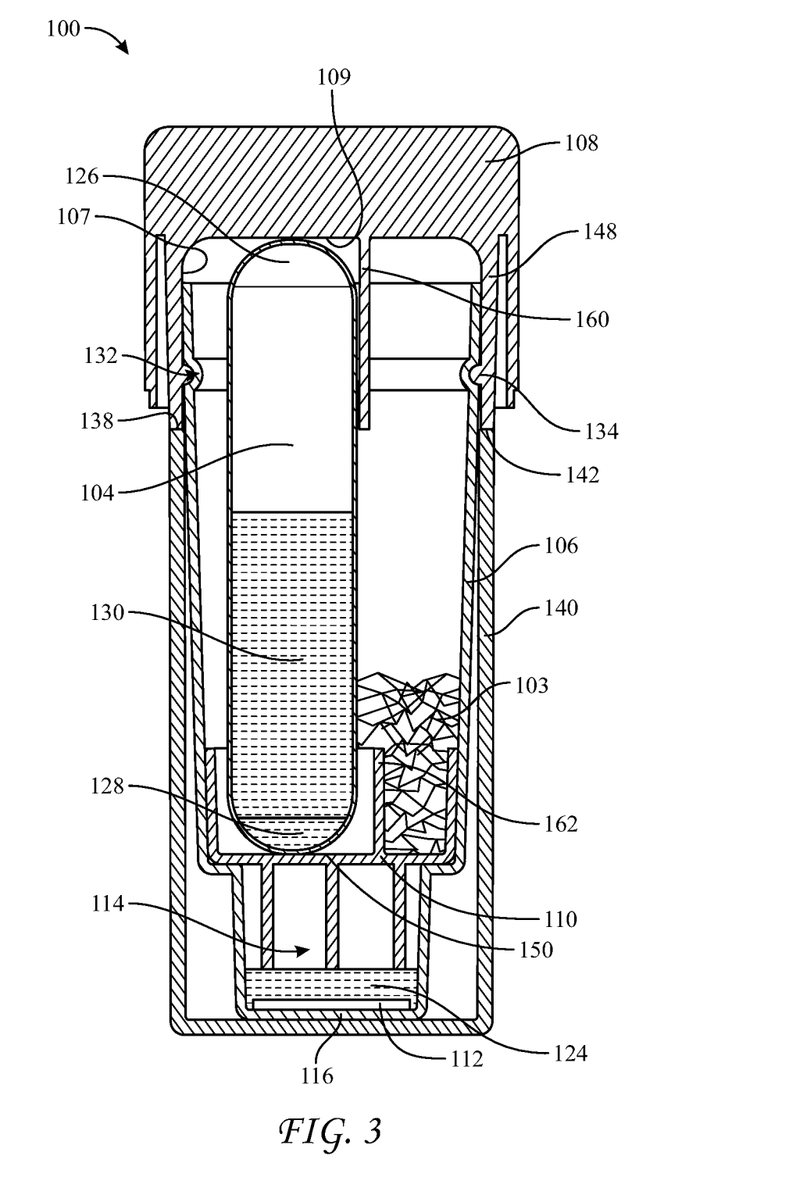
FIG. 3 depicts a cross-sectional view of the self-contained biological indicator of FIG. 1 with the cap in a second position.

Further, to facilitate accidental advancement of cap 108 from the unactivated position directly to the third position without stopping at the second position, various features may be incorporated to facilitate stopping cap 108 at the second position. In some embodiments, tongue and groove features may be incorporated into vial 106 and cap 108. For example, vial 106 may include an annular groove 132 near to its top. An annular tongue 134 on an inner side surface 107 of annular projection 148 of cap 108 seats within annular groove 132. Accordingly, cap 108 may be fabricated from a material that it is somewhat flexible and resilient such that annular projection 148 may be in a somewhat expanded configuration prior to activation, i.e., when tongue 134 is not seated within groove 132. However, as shown in FIG. 3, when tongue 134 is aligned with groove 132, tongue 134 seats within groove 132 such that annular projection 148 is not in an expanded configuration. Further, when tongue 134 is seated within groove 132, cap 108 is in the second position and first ampule 102 should be broken, leaving behind shards 103 and permitting growth medium 124 to flow into growth reservoir 114 to submerge spore disk 112. Second ampule 104, however, should not be broken because when cap 108 is disposed in the second position, inner top surface 109 of cap 108 is disposed above second top 126 of second ampule 104. In some embodiments, a second groove (not shown) may be included on the vial into which tongue 134 seats when cap 108 is in the third position. In some embodiments, cap 108 may include a groove and vial 106 may include a tongue.

In other embodiments, SCBI 100 may alternatively or additionally include a stop surface 138, e.g., on a second vial or "counter cap" 140. Counter cap 140 may have the form of a cylindrical vial or capsule that may fit over or be disposed about vial 106 such that stop surface 138 is concentrically disposed about a circumferential portion of vial 106 and further disposed between approximately 0.1 inches and 1.5 inches below a rim 142 of cap 108. So disposed, surface 138 prevents inner top surface 109 of cap 108 from contacting second top 126 of second ampule 104. Upon depression of cap 108 from the first position, cap 108 may be advanced until rim 142 of cap 108 contacts stop surface 138, at which point cap 108 is in the second position. Stop surface 138 prevents further downward movement of cap 108. Accordingly, when counter cap 140 is disposed over vial 106, cap 108 may be depressed to break first ampule 102, but not second ampule 104. Following breakage of first ampule 102, counter cap 140 may be removed from about vial 106 thereby permitting a healthcare worker to place SCBI 100 into a reader or to depress cap 108 to the third position to break second ampule 104.

Figure 4:
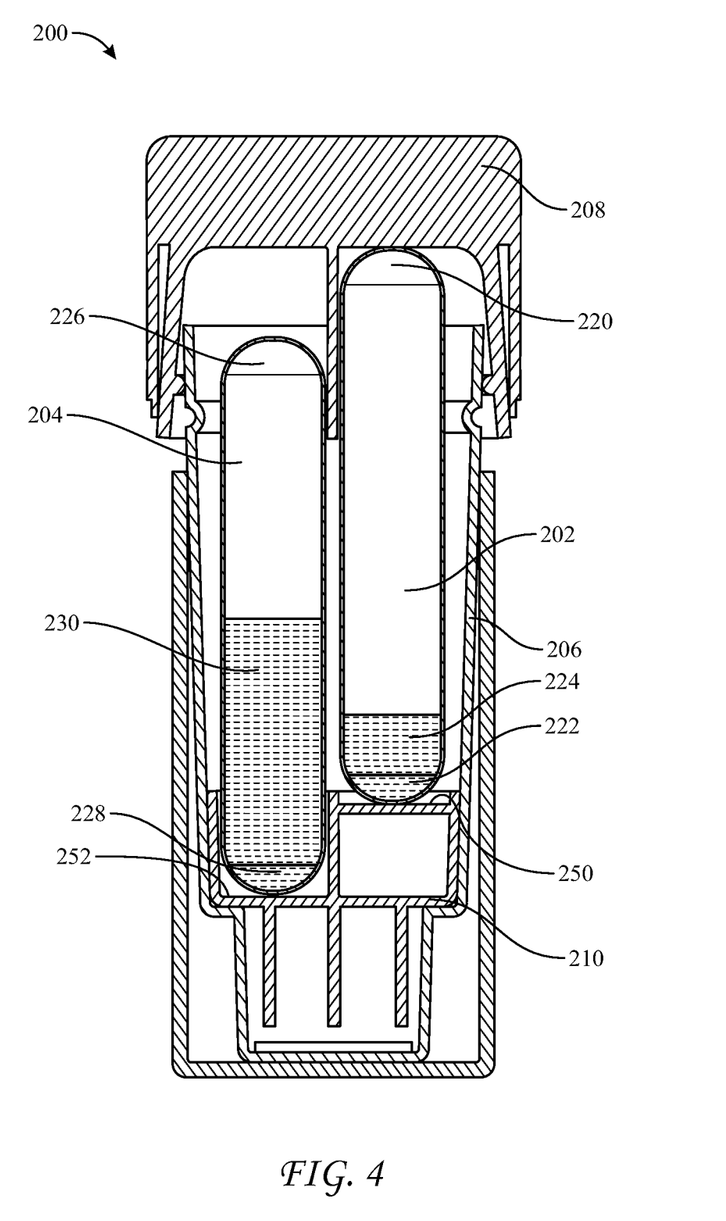
FIG. 4 depicts a cross-sectional view of an alternative embodiment of a self-contained biological indicator.

FIG. 4 shows an alternate embodiment of an SCBI in accordance with the present subject matter. SCBI 200 includes a first ampule 202, a second ampule 204, a vial 206, a cap 208, and an insert 210. Similar to SCBI 100, first top 220 of first ampule 202 is closer to cap 208 than second top 226 of second ampule 204. First ampule 202 and second ampule 204 may be identical or of substantially the same volume to each other, although the amounts and types of first growth medium 224 and 230 that they respectively contain may be different. Insert 210 may enable such a design because it includes two surfaces, a first surface 250 and a second surface 252 that is offset from first surface 250. In some embodiments, first surface 250 may be disposed between 0.1 inches and 1.5 inches above second surface 252. In some embodiments, first surface 250 may be disposed approximately 0.8 inches above second surface 252. First bottom 222 of first ampule 202 contacts first surface 250 of insert 220 and second bottom 228 of second ampule 204 contacts second surface 252 of insert 220. Accordingly, even when first ampule 202 and second ampule 204 are identical to each other, first top 220 is disposed closer to cap 208 than second top 226, thereby enabling first ampule 202 to be broken before second ampule 204.

An SCBI fabricated in accordance with the present subject matter may be used to determine whether a sterilization cycle was efficacious according to a first mode of fluorescence analysis and a second mode of visual interpretation for color change. Although the following exemplary method refers to SCBI 100, it should be understood that an SCBI of another embodiment, e.g., SCBI 200, may be utilized in the method. First, SCBI 100 may be subject to a sterilization process. Second SCBI 100 may be activated by depressing cap 108 to displace cap 108 relative to vial 106 from an unactivated position or a first position to the second position. Third, first ampule 102 may be broken by pressures associated with depressing cap 108 from the first position toward the second position. Fourth, SCBI 100 may be placed into a reading device. Fifth, SCBI 100 may be analyzed for changes in fluorescence of first growth medium 124. Sixth, SCBI 100 may be removed from the reading device. Seventh, cap 108 may be depressed to further displace cap 108 relative to vial 106, i.e., from the second position toward the third position. Eighth, second ampule 104 may be broken by pressures associated with depressing cap 108 from the second position to the third position. Ninth, SCBI 100 may be analyzed by visual interpretation for changes in color of second growth medium 130.

Some exemplary methods may also include the following steps between the third and fourth steps. Tenth, cap 108 may be positioned such that groove 132 mates with tongue 134. Eleventh, tongue 134 may be removed from groove 132. Alternatively or additionally, the following steps may be performed between the third and fourth steps. Twelfth, rim 142 of cap 108 may be positioned against counter cap 140. Thirteenth, counter cap 140 may be removed from vial 106.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometries, materials, dimensions, ratios, steps, and the like discussed above are illustrative. Accordingly, the claims should not be limited to the specific details of structure and operation set forth in the written description and drawings.

We claim:

1. A self-contained biological indicator, comprising:
   a first ampule having a first top and a first bottom, the first ampule containing a first volume of a first growth medium;
   a second ampule having a second top and a second bottom, the second ampule containing a second volume of a second growth medium;
   a cap,
   a vial coupled to the cap and containing at least a portion of the first ampule and a portion of the second ampule, and
   a counter cap disposed about the vial, the counter cap including a stop surface disposed between 0.1 inches and 1.5 inches below a rim of the cap,
   wherein the cap is disposed above the first ampule and the second ampule, the first ampule is disposed adjacent to the second ampule, and the first top is disposed closer to the cap than the second top.

2. The self-contained biological indicator of claim 1 further comprising an insert, wherein at least a portion of the insert is disposed below the first ampule and the second ampule, and the first bottom and the second bottom contact the insert.

3. The self-contained biological indicator of claim 1, wherein the first ampule is longer than the second ampule.

4. The self-contained biological indicator of claim 3, wherein the first ampule is between 0.5 inches and 1.5 inches longer than the second ampule.

5. The self-contained biological indicator of claim 4, wherein the first ampule is 1 inch longer than the second ampule.

6. The self-contained biological indicator of claim 2, wherein the insert includes a first surface and a second surface further from the cap than the first surface, and wherein the first bottom contacts the first surface and the second bottom contacts the second surface.

7. The self-contained biological indicator of claim 6, wherein the first surface is disposed between 0.1 inches to 1.5 inches above the second surface.

8. The self-contained biological indicator of claim 7, wherein the first surface is disposed 0.8 inches above the second surface.

9. The self-contained biological indicator of claim 1, wherein the first top contacts the cap.

10. The self-contained biological indicator of claim 1, wherein the first growth medium is the same as the second growth medium.

11. The self-contained biological indicator of claim 10, wherein the first growth medium and the second growth medium include 4-methylumbelliferyl α-D-glucoside (MUG).

12. The self-contained biological indicator of claim 1, wherein the first volume is less than the second volume.

13. The self-contained biological indicator of claim 12, wherein the first volume is between 50 µl and 150 µl and the second volume is greater than approximately 150 µl.

14. The self-contained biological indicator of claim 13 wherein the first volume is 100 µl and the second volume is 300 µl.

15. The self-contained biological indicator of claim 1, wherein the vial and the cap are coupled by a tongue and a groove.

16. The self-contained biological indicator of claim 1, wherein the stop surface is disposed 0.8 inches from the rim of the cap.

* * * * *